United States Patent
Fujii et al.

(10) Patent No.: US 7,192,770 B2
(45) Date of Patent: Mar. 20, 2007

(54) SCREENING FOR SKIN WRINKLING MODULATORS

(75) Inventors: Seishiro Fujii, Boston, MA (US); Paolo Dotto, Boston, MA (US); Rong Han, Boston, MA (US); Janice Brissette, Charlestown, MA (US)

(73) Assignee: The General Hospiatal Corporation, Boston, MA (US)

( * ) Notice: Subject to any disclaimer, the term of this patent is extended or adjusted under 35 U.S.C. 154(b) by 255 days.

(21) Appl. No.: 10/664,795

(22) Filed: Sep. 19, 2003

(65) Prior Publication Data

US 2004/0110203 A1 Jun. 10, 2004

Related U.S. Application Data

(60) Provisional application No. 60/412,503, filed on Sep. 20, 2002.

(51) Int. Cl.
C12N 5/00 (2006.01)

(52) U.S. Cl. .......................... 435/375; 514/844

(58) Field of Classification Search .................. 435/4, 435/375; 514/844, 887
See application file for complete search history.

(56) References Cited

U.S. PATENT DOCUMENTS

| 5,753,263 | A | 5/1998 | Lishko et al. |
| 6,224,901 | B1 | 5/2001 | Li et al. |
| 6,299,858 | B1 | 10/2001 | Serbedzija et al. |

OTHER PUBLICATIONS

Weinberg W. et al. p21 Control of Epithelial Cell Cycle and Cell Fate. Critical Review of Oral Biology Medicine 2002 13(6)453-464.*
Di Cunto et al., "Inhibitory Function of $p21^{Cip1/WAF1}$ in Differentiation . . . ", May 15, 1998, Science, vol. 280;1069-1072.
G. Paolo Dotto, "$p21^{WAF1/Cip1}$: more than a break to the cell cycle?", 2000, Biochimica et Biophysica Acta 1471;M43-M56.
Missero et al., "Involvement of the cell-cycle inhibitor *CIP1/WAF1* and the . . . ", Jun. 1995, Proc. Natl. Acad. Sci., vol. 92;5451-5455.
Missero et al., "The absence of $p21^{Cip1/WAF1}$ alters keratinocyte growth . . . ", 1996, Genes & Development, vol. 10;3065-3075.
Oh et al., "Negative regulation of cell growth and differentiation by TSG101 . . . ", Apr. 16, 2002, PNAS, vol. 99(8);5430-5435.
Prowse et al., "Involvement of the Sp3 Transcription Factor in Induction . . . ", 1997, J. Biological Chem., vol. 272(2);1308-1314.
Rangarajan et al., "Notch signaling is a direct determinant of keratinocyte . . . ", 2001, The EMBO Journal, vol. 20(13);3427-3436.
Santini et al., "Cross talk among calcineurin, Sp1/Sp3, and NFAT in control of $p21^{WAF1/Cip1}$ expression . . . ", Aug. 14, 2004, PNAS, vol. 98(17);9575-9580.
Topley et a;., "$p21^{WAF1/Cip1}$ functions as a suppressor of malignant skin tumor formation . . . ", Aug. 1999, Proc. Natl. Acad. Sci., vol. 96;9089-9094.

* cited by examiner

*Primary Examiner*—Ralph Gitomer
(74) *Attorney, Agent, or Firm*—Fish & Richardson P.C.

(57) ABSTRACT

The invention features methods of screening for compounds that prevent and/or reduce UVB-induced skin damage, e.g., wrinkles. The method includes identifying an agent that increases or induces the expression, activity or levels of a component of the p21 signal transduction pathway. Also included are methods and compositions for treating UVB-induced skin damage.

9 Claims, No Drawings

SCREENING FOR SKIN WRINKLING MODULATORS

RELATED APPLICATIONS

This application claims the benefit of U.S. Provisional Application 60/412,503, filed Sep. 20, 2002, the contents of which are incorporated herein by reference.

BACKGROUND OF THE INVENTION p21 (a downstream effector of p53) is believed to function as tumor suppressor. The p21 signal transduction pathway, including p53, p21, cyclin/CDK complex, p300, CBP, NFkB, Sp1, SP3, Notch 1 and PCNA, has been implicated in cell cycle control and apoptosis. Therefore, this pathway is an established target for cancer therapy (reviewed by Dotto (2000) *Biochim. Biophys. Acta* 1471:M43–M56). p21 has also been implicated in keratinocyte differentiation (Topley et al. (1999) *Proc. Nat. Acad. Sci. USA* 96:9089; Missero et al (1995) *Proc. Nat. Acad. Sci. USA* 92:5451; Missero et al. (1996) *Genes & Devel.* 10:3065; Prowse et al (1997)*J. Biol. Chem.* 272:1308; Di Cunto et al. (1998) *Science* 280:1069; Rangarajan et al. (2001) *EMBO J.* 20:3427; Santini et al. (2001) *Proc. Nat. Acad. Sci. USA* 98:9575).

SUMMARY OF THE INVENTION

The invention is based, in part, on the inventors' discovery that the p21 signal transduction pathway is important for the maintenance and/or appearance of skin. In particular, the inventors have found that the p21 signal transduction pathway is important in the prevention of skin damage, e.g., UVB-induced skin damage, e.g., for the prevention, reduction or treatment of wrinkles. Therefore, the inventors have identified the p21 signal transduction pathway as a target for screening and treatment methods for the prevention and/or reduction of UVB-induced skin damage, e.g., the prevention and/or reduction of UVB-induced wrinkles. The invention thus features screening and treatment methods for prevention or reduction of UVB-induced wrinkles, and related composition, e.g., cosmetic compositions.

Accordingly, in one aspect, the invention features a method of screening for an agent that prevents and/or reduces UVB-induced skin damage, e.g., wrinkles. The method includes identifying an agent that increases or induces the expression, activity or levels of a component of the p21 signal transduction pathway, e.g., p21, p53, cyclin/CDK complex, p300, CBP, NFkB, Notch1, Sp1, or Sp3, but preferably p21.

The method can also include correlating increased expression, activity or levels of a component of the p21 signal transduction pathway with the agent's ability to prevent or reduce wrinkles, e.g., identifying the identified agent as a wrinkle protection or reduction agent (e.g., providing print material or a computer readable medium, e.g., informational, marketing or instructional print material or computer readable medium, related to the identified agent or its use). Correlating means identifying a test agent that increases expression, activity or levels of a component of the p21 signal transduction pathway (and preferably increases p21 expression, levels or activity) as an agent capable of preventing, reducing or treating wrinkles. The correlating step can include, e.g., generating or providing a record, e.g., a print or computer readable record, such as a laboratory record or dataset or an email, identifying a test agent that increases expression, activity or levels of a component of the p21 signal transduction pathway (and preferably increases p21 expression, levels or activity) as an agent capable of preventing, reducing or treating wrinkles. The record can include other information, such as a specific test agent identifier, a date, an operator of the method, or information about the source, structure, method of purification or biological activity of the test agent. The record or information derived from the record can be used, e.g., to identify the test agent as a compound or candidate agent (e.g., a lead compound) for pharmaceutical or therapeutic use. The identified agent can be identified as an agent or a potential agent for treatment or reduction or wrinkles. Agents, e.g., compounds, identified by this method can be used, e.g., in the treatment (or development of treatments, e.g., cosmetic treatments) for wrinkles.

In one embodiment, the method includes evaluating, e.g., measuring, the effect of the agent on skin, e.g., evaluating a parameter correlated with wrinkles, e.g., the presence, extent, or type of wrinkles; and selecting an agent from the screen, .g., an agent that prevents or reduces damage to the skin, e.g., prevents or reduces wrinkles in the skin. Preferably, evaluating the effect of the agent on skin includes administering the agent, e.g., topically, to a tissue or subject and comparing a parameter correlated with wrinkles, e.g., the presence, extent, or type of wrinkles in the tissue or subject, optionally with a reference value, e.g., a control or baseline value, e.g., a value for the same parameter in a tissue or subject that has been treated differently, e.g., has not been administered the agent. The effect of the agent on skin can be evaluated in the absence or presence of a source of skin damage, e.g., an agent or treatment that induces wrinkle formation, e.g., UVB radiation. In some embodiments, the evaluation includes entering a value for the evaluation, e.g., a value for the presence, extent, or type of wrinkles into a database or other record.

In a preferred embodiment, the agent is evaluated for the ability to prevent or reduce UVB-induced wrinkles.

In a preferred embodiment, the subject is an experimental animal, e.g., a wildtype or transgenic experimental animal, e.g., a rodent, e.g., a rat, mouse or guinea pig. The subject can also be a human. In a preferred embodiment, the evaluating step comprises administering the agent to the skin of the subject, e.g., topically.

In a preferred embodiment, an agent that increases or induces the expression, activity or level of p21 is identified.

In a preferred embodiment, the identifying step includes: (a) providing a cell, tissue or non-human animal harboring an exogenous nucleic acid that includes a regulatory region (e.g., a promoter) of a component of the p21 signal transduction pathway operably linked to a nucleotide sequence encoding a reporter polypeptide (e.g., a light based, e.g., colorimetric or fluorescently detectable label, e.g., a fluorescent reporter polypeptide, .g., GFP, EGFP, BFP, RFP); (b) evaluating the ability of a test agent to increase the activity of the reporter polypeptide in the cell, tissue or non-human animal; and (c) selecting a test agent that increases the activity of the reporter polypeptide as an agent that increases or induces a component of the p21 signal transduction pathway. In one embodiment, the cell or tissue is a skin cell or tissue, e.g., a keratinocyte cell or tissue, e.g., a skin explant. In another embodiment, the non-human animal is a transgenic animal, e.g., a transgenic rodent, e.g., a mouse, rat or guinea pig, harboring the nucleic acid. In one embodiment, the component of the p21 signal transduction pathway is p21.

In one embodiments, the method includes two evaluating steps, e.g., the method includes a first step of evaluating the test agent in a first system, e.g., a cell or tissue system, and a second step of evaluating the test agent in a second system, e.g., a second cell or tissue system or in a non-human animal. In other embodiments, the method includes two evaluating steps in the same type of system, e.g., the agent is re-evaluated in a non-human animal after a first evaluation in the same or a different non-human animal. The two evaluations can be separated by any length of time, e.g., days, weeks, months or years.

In a preferred embodiment, the effect of the agent on UVB-induced wrinkles is evaluated. For example, the agent is evaluated before, during and/or after UVB exposure.

The agent that increases or induces the expression, activity or levels of a component of the p21 signal transduction pathway, e.g., p21, can be a crude or semi-purified extract, e.g., an organic, e.g., animal or botanical extract, or an isolated compound, e.g., a small molecule, protein, lipid or nucleic acid. Particularly preferred are naturally occurring substances or extracts, e.g., plant or fungal extracts. For example, the agent can be any of: (a) a polypeptide component of the p21 signal transduction pathway, e.g., a p21 polypeptide or a functional fragment or mimetic thereof; (b) a peptide or protein agonist of a component of the p21 signal transduction pathway that increases an activity of the p21 signal transduction pathway, e.g., increases p21, p53, cyclin/CDK complex formation or nuclear localization, p300, CBP, NFkB, Sp1, or Sp3; (c) a small molecule that increases expression of a component of the p21 signal transduction pathway, e.g., p21, p53, cyclin/CDK complex, p300, CBP, NFkB, Sp1, and Sp3, e.g., by binding to the promoter region of its gene; (d) an antibody, e.g., an antibody that binds to and stabilizes or assists the binding of a p21 pathway component to a binding partner, e.g., the binding of p21 to cyclin/CDK; (e) a chemical compound, e.g., an organic compound, e.g., a naturally occurring or synthetic organic compound that increases expression of a component of the p21 signal transduction pathway, e.g., p21, p53, cyclin/CDK complex, p300, CBP, NFkB, Sp1, and Sp3; or (f) a nucleotide sequence encoding a p21 pathway polypeptide or functional fragment or analog thereof. The nucleotide sequence can be a genomic sequence or a cDNA sequence. The nucleotide sequence can include: a p21 pathway component coding region; a promoter sequence, e.g., a promoter sequence from a p21 pathway component gene or from another gene; an enhancer sequence; untranslated regulatory sequences, e.g., a 5' untranslated region (UTR), e.g., a 5'UTR from a p21 gene or from another gene, a 3' UTR, e.g., a 3'UTR from a p21 gene or from another gene; a polyadenylation site; an insulator sequence. In another preferred embodiment, the level of a component of the p21 signal transduction pathway, e.g., p21, p53, cyclin/CDK complex, p300, CBP, NFkB, Sp1, or Sp3 is increased by increasing the level of expression of an endogenous component of the p21 signal transduction pathway, e.g., p21, p53, cyclin/CDK complex, p300, CBP, NFkB, Sp1, or Sp3 gene, e.g., by increasing transcription of the p21 gene or increasing p21 mRNA stability. In a preferred embodiment, transcription of the p21 gene is increased by: altering the regulatory sequence of the endogenous factor p21 gene, e.g., in a somatic cell, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the p21 gene to be transcribed more efficiently. In a preferred embodiment, the agent is in a crude or partially purified botanical extract.

In another aspect, the invention features a method of treating skin, e.g., preventing or reducing wrinkles. The method includes (a) identifying a subject in need of prevention or treatment of wrinkles; and (b) increasing or inducing a component of the p21 signal transduction pathway in the subject, e.g., administering to the subject an effective amount of an agent that increases or induces the activity, level or expression of a component of the p21 signal transduction pathway, e.g., an agent described herein. Preferably, the agent is administered to the subject's skin, e.g., topically. The agent can be administered to the face, chest, neck, hands, and other regions of the body. The treatment can involve more than one administration, e.g., at least two, three, or four administrations, of the agent. The treatment can also involve daily administration of the agent.

In a preferred embodiment, the agent increases or induces the expression, level or activity of p21.

In a preferred embodiment, the subject has been or will be exposed to UVB radiation.

In a preferred embodiment, the method includes evaluating the effect of the administration on the wrinkle.

The identification of a subject in need of preventing or reducing wrinkles can be performed e.g., by the subject, by a health care provider, or by a provider of cosmetics. The agent may be administered, e.g., by the subject, by a health care provider, or by a provider of cosmetics. Likewise, the evaluation of the effect of wrinkle formation may be performed, e.g., by the subject, by a health care provider, or by a provider of cosmetics.

In another aspect, the invention also features compositions containing an agent that increases or induces the expression activity, or level of a component of the p21 signal transduction pathway, e.g., p21, for preventing or reducing wrinkles, e.g., UVB-induced wrinkles, e.g., an agent described herein, e.g., an agent identifying by a screening method described herein. In a preferred embodiment, the agent is provided in a pharmaceutically acceptable composition. In a preferred embodiment, the composition is sterile. The composition is effective to prevent or reduce the appearance of wrinkles (e.g., temporarily) when applied to the skin, e.g., for a period of at least 1 to 100 days, more preferably at least 7 to 90 days, even more preferably 14 to 60 days, or it can be effective to prevent or reduce the appearance of wrinkles for a longer term, e.g., at least 3 to 9 months, more preferably 4 to 8 months, or about 6 months. In a preferred embodiment, the composition also has a fragrance, a preservative, or other cosmetic ingredient, e.g., a moisturizer, or sunscreen agent, e.g., octyl methoxycinnamate, aminobenzoic acid, oxybenzone, padimate O, homosalate, or titanium dioxide. The composition can be provided in an oil, cream, lotion, foam, gel, or other cosmetic preparation.

In another aspect, the invention features a method of providing wrinkle protection to a subject by supplying to the subject a composition containing an agent that increases or induces the expression activity, or level of a component of the p21 signal transduction pathway, e.g., p21, e.g., an agent described herein, e.g., an agent identified by a screening method described herein, preferably with instructions to apply prior to, or after, UV exposure, e.g., UVB, e.g., sunlight exposure.

In another aspect, the invention features a kit for providing wrinkle protection to a subject which includes a composition described herein, e.g., a composition containing an agent that increases or induces the expression activity, or level of a component of the p21 signal transduction pathway, e.g., p21; and instructions for use, e.g., instructions to apply the composition prior to, or after, UV, e.g., UVB exposure, e.g., sunlight exposure.

An effective amount of the agent of the present invention is defined as the amount of a composition which, upon administration to a subject, prevents the formation of wrinkles in the subject, or reduces the appearance of wrinkles in the subject. The effective amount to be administered to a subject is typically based on a variety of factors including age, sex, surface area, weight, and conditions of the skin. Body surface area may be approximately determined from height and weight of the patient. See, e.g., Scientific Tables, Geigy Pharmaceuticals, Ardley, N.Y., 1970, 537. Effective doses will vary, as recognized by those skilled in the art, dependant on route of administration, excipient usage, and the possibility of co-usage with other treatments such as usage of other wrinkle reducing compounds.

As used herein, "preventing or reducing wrinkles" means the application or administration of a therapeutic agent to a subject who has a wrinkle or has a predisposition toward wrinkles, or who has been exposed to an agent likely to cause wrinkles, e.g., UV radiation, e.g., UVB irradiation, with the purpose to prevent, reduce, improve, alleviate, alter, remedy, ameliorate, or affect, the appearance of the wrinkle or the formation of the wrinkle. The compound of the invention can be administered to the subject by the subject himself or herself, or by another person, e.g., a health care provider or a provider of cosmetics. In preferred embodiments of the methods described herein, wrinkles, e.g., fine wrinkles, are prevented or reduced in the subject by at least 5%, preferably at least 10%, more preferably at least 20%, 25% or more.

The methods and compositions can be used prophylactically (e.g., before wrinkles are apparent) or they can be used to prevent further wrinkle formation or reduce the appearance of wrinkles in a subject. The use of the composition for the manufacture of a medicament or cosmetic for preventing or treating wrinkles is also within the scope of this invention.

DETAILED DESCRIPTION

The inventors have identified the p21 signal transduction pathway as a target for screening and treatment methods and related cosmetic compositions for prevention and/or reduction of UVB-induced skin damage, e.g., prevention and/or reduction of wrinkles.

Wrinkles

Wrinkles are generally a result of the natural aging process of the skin, and of exposure to the sun's ultraviolet rays. A wrinkle is a configuration change in the surface of the skin, without specific structural alterations at the histological level. Generally, wrinkles are classified as described in Kligman et al. (1985) *Br J Derm* 113 :37–42, herein incorporated by reference. Kligman classifies wrinkles into three classes: linear wrinkles, glyphic wrinkles, and crinkles. Linear wrinkles are straight, found generally in the facial skin, and are caused by natural aging or exposure to ultraviolet light. Glyphic wrinkles are shaped as apparent triangles or rectangles of wrinkles, are found on the face, hands, and neck exposed to sunlight, and are aggravated by exposure to ultraviolet light or dermatoheliosis. Crinkles are thin, crinkled wrinkles on flabby skin, found anywhere on the skin, but typically on the backs of hands and around the eyelids.

The effect of a compound on the formation or appearance of wrinkles can be evaluated qualitatively, e.g., by visual inspection, or quantitatively, e.g., by microscopic or computer assisted measurements of wrinkle morphology. Preferably, wrinkle morphology is quantitatively analyzed, e.g., the number, depth, length, area, volume and/or width of wrinkles per unit area of skin are measured. Examples of quantitative methods for measuring wrinkles include, but are not limited to, the optical cut technique employing a laser beam, as proposed by Hoshino (1992) *Pixel* 45:121, herein incorporated by reference; or methods which analyze three-dimensional skin replicas, e.g., the Shiseido Wrinkle Analyzer 3D Pro system (Takasu et al. (1996) *J Soc Cosmet Chem Japan* 29:394–405).

Methods of Screening

The p21 signal transduction pathway, including p53, p21, cyclin/CDK complex, p300, CBP, NFkB, Sp1, and Sp3, is well characterized. The components of the pathway have been cloned, and their protein and gene sequences are readily available to one of ordinary skill in the art. For example, cloning of p21 cDNA and gene was described in Xiong et al. (1993) *Nature* 366(6456):701–4; GenBank Accession Nos. S67388, AAB29246, and NM_078467). p21 reporter constructs have been described, e.g., in Datto et al. (1995) J. Biol. Chem. 270, 28623–28628.

Numerous methods exist for evaluating whether an agent alters expression or activity or level of a particular protein. In one embodiment, the ability of a test agent to modulate (e.g., increase or decrease) (e.g., permanently or temporarily) expression from a p21 promoter is evaluated by e.g., routine reporter (e.g., LacZ or GFP) transcription assay. For example, a cell or transgenic animal whose genome comprises a reporter gene operably linked to a p21 promoter, can be contacted with a test agent, and the ability of the test agent to increase or decrease reporter activity is indicative of the ability of the agent to modulate pigmentation. In another embodiment, the ability of a test agent to modulate p21 expression, or p21 activity or level is evaluated in a transgenic animal, for example, a transgenic animal described herein. The effect of a test agent on p21 expression or p21 activity or level may be evaluated on a cell or cell lysate, or subject, preferably a non-human experimental mammal, and more preferably a rodent (e.g., a rat, mouse, rabbit), or explant (e.g., skin) thereof. Numerous methods of assessing p21 expression are well know in the art, e.g., Northern analysis, ribonuclease protection assay, reverse transcription-polymerase chain reaction (RT-PCR) or RNA in situ hybridization (see, e.g., Sambrook et al. *Molecular Cloning: A Laboratory Manual* ($3^{rd}$ ed. 2001)). The level of p21 may be monitored by, e.g., Western analysis, immunoassay, or in situ hybridization. p21 activity (e.g. altered promoter binding and/or transcription activity) may be determined by, e.g., electrophoretic mobility shift assay, DNA footprinting or reporter gene assay. Preferably, the effect of a test agent on p21 expression or p21 activity or level is evaluated on a transgenic cell or non-human animal, or explant or cell derived therefrom.

Test Agents

Agents to be tested in the screening methods described herein include crude or purified extracts of organic sources, e.g., animal or botanical extracts, as well as partially or fully purified or synthetic agents, e.g., small molecules, polypeptides, lipids and/or nucleic acids, ad libraries of these. Agents that have been previously identified as inducers of p21 or p53 tumor suppressor activity useful as cancer therapeutics can be tested and/or used in the wrinkle-related methods and compositions described herein.

Administration

The composition for the prevention or reduction of wrinkles may be administered via the parenteral route, including orally, topically, subcutaneously, intraperitoneally, intramuscularly, intranasally, and intravenously. Topical administration is preferred. Repeated administration of the composition, e.g., repeated topical administration, can be used. More than one route of administration can be used simultaneously, e.g., topical administration in association with oral administration. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the wrinkle reducing composition.

The composition of this invention can also be formulated into dosage forms for other routes of administration utilizing conventional methods. A pharmaceutical composition can be formulated, for example, in dosage forms for oral administration in a capsule, a tablet (each including timed release and sustained release formulations), or a gel seal. Capsules may comprise any standard pharmaceutically acceptable material such as gelatin or cellulose derivatives. Tablets may be formulated in accordance with the conventional procedure by compressing mixtures of p21 inducing compounds and a solid carrier, and a lubricant. Examples of solid carriers include starch and sugar bentonite. The wrinkle reducing composition can also be administered in a form of a hard shell tablet or capsule containing, for example, lactose or mannitol as a binder and a conventional filler and a tableting agent.

Topical administration of the wrinkle reducing compounds described herein presents a preferred route of administration amongst the many different routes described above. For topical application, the compositions of the present invention can include a medium compatible with skin. Such topical pharmaceutical compositions can exist in many forms, e.g., in the form of a solution, cream, ointment, gel, lotion, shampoo, or aerosol formulation adapted for application to the skin. A wide variety of carrier materials can be employed in the wrinkle reducing composition of this invention such as alcohols, aloe vera gel, allantoin, glycerine, vitamin A and E oils, mineral oils, and polyethylene glycols. Other additives, e.g., preservatives, fragrance, sunscreen, or other cosmetic ingredients, can be present in the composition. The topical composition can be applied and removed immediately, or it can be applied and left on the skin surface, e.g., the face, for an extended period of time, e.g., overnight or throughout the day.

Kits

An agent, e.g., an agent identified through a method described herein, can be provided in a kit. The kit includes (a) the agent, e.g., a composition that includes the agent, and (b) informational material. The informational material can be descriptive, instructional, marketing or other material that relates to the methods described herein and/or the use of the agent for the methods described herein. For example, the informational material relates to wrinkles or their prevention or reduction.

In one embodiment, the informational material can include instructions to administer the agent in a suitable manner to perform the methods described herein, e.g., in a suitable dose, dosage form, or mode of administration (e.g., a dose, dosage form, or mode of administration described herein). A preferred dose, dosage form, or mode of administration is topical, e.g., on the skin. In another embodiment, the informational material can include instructions to administer the agent to a suitable subject, e.g., a human, e.g., a human having, or at risk for, wrinkles. For example, the material can include instructions to administer the agent to the face, neck or hands.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about the agent and/or its use in the methods described herein. Of course, the informational material can also be provided in any combination of formats.

In addition to the agent, the composition of the kit can include other ingredients, such as a solvent or buffer, a stabilizer, a preservative, a fragrance or other cosmetic ingredient, and/or a second agent for treating a condition or disorder described herein, e.g., a sunscreen. Alternatively, the other ingredients can be included in the kit, but in different compositions or containers than the agent. In such embodiments, the kit can include instructions for admixing the agent and the other ingredients, or for using the agent together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent. For example, the kit includes a plurality of syringes, ampules, foil packets, or blister packs, each containing a single unit dose of the agent. The containers of the kits can be air tight and/or waterproof.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device.

The following specific examples, which describe the wrinkle reducing compositions of this invention and biological testings of such compositions, are to be construed as merely illustrative, and not limitative of the remainder of the disclosure in any way whatsoever.

EXAMPLES

Example 1 p21 Knock Out Mice Show Increased Wrinkle Formation

Wildtype and p21 knockout female mice (eight weeks of age) were clipped of hair, then irradiated with UVB (cumulative UVB dose: 6.4 J/cm$^2$). Wildtype mice not subjected to UVB radiation were used as a control. Mice were evaluated for the extent of wrinkle formation, and assigned to one of each of 5 categories, as follows: 0, no wrinkle; 1, slight wrinkles; 2, clear wrinkles; 3, strong wrinkles, 4, severe wrinkles (Table 1, n=2). Long term UVB irradiation produced pronounced wrinkle formation in p21 deficient female mice, as compared with wildtype mice.

TABLE 1

|  | mouse A | mouse B | average |
|---|---|---|---|
| p21 knockout female + UVB | 3 | 4 | 3.5 |
| wildtype female + UVB | 1 | 1 | 1.0 |
| wildtype female, no UVB | 0 | 0 | 0 |

More wrinkling was observed in p21 knock out mice, as compared with wildtype and non-irradiated mice. Histological analysis showed accumulation of inflammatory cells in the upper dermis and elastic tissues in the dermis in p21 knock out mice, as compared with wild and non-irradiated wild mice.

Example 2 p21 Knock Out Mice Show More Inflammation by UVB Irradiation

Ear swelling response after UVB irradiation (112 mJ/cm$^2$) was evaluated in male mice (8weeks of age, n=3). Ear thickness was measured by a standard thickness gage (Mitsutoyo Corp.). The results are shown in Table 2.

TABLE 2

|  | Day | | | | | |
|---|---|---|---|---|---|---|
|  | 0 | 1 | 2 | 3 | 4 | 5 |
| p21 knockout | 100% | 125.2% | 131.5% | 182.0% | 233.4% | 265.9% |
| wildtype male | 100% | 135.8% | 145.6% | 147.6% | 156.4% | 161.9% |

More swelling was observed after UVB irradiation in p21 knock out mice, as compared with wildtype mice.

Example 3 p21 Knock Out Mice Show Increased Wrinkle Formation

Female mice enter the third hair cycling in the UVB irradiated period (8 weeks–18 weeks of age). Male mice are an alternate model for long term UVB irradiation, because they do not enter the third hair cycle in the irradiation period. Male mice (eight weeks of age) were clipped of hair, then irradiated with UVB. Long term UVB irradiation (cumulative UVB dose: 1.4 J/cm$^2$) produced pronounced wrinkle formation in p21 deficient male mice, as compared with wildtype mice (Table 3, n=4). Mice were evaluated for the extent of wrinkle formation, and assigned to one of each of 5 categories, as follows: 0, no wrinkle; 1, slight wrinkles; 2, clear wrinkles; 3, strong wrinkles, 4, severe wrinkles.

TABLE 3

|  | Mouse A | Mouse B | Mouse C | Mouse D | average |
|---|---|---|---|---|---|
| p21 knockout male + UVB | 1 | 1 | 3 | 3 | 2.0 |
| wildtype male + UVB | 1 | 0 | 1 | 0 | 0.5 |
| wildtype male, no UVB | 0 | 0 | 0 | 0 | 0 |

Histological analysis showed increased accumulation of inflammatory cells in the upper dermis and elastic tissues and fibers in the dermis in p21 knock out mice, as compared with wildtype and non-irradiated wild mice.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of screening for an agent that reduces the appearance or formation of wrinkles, the method comprising:
    providing a test agent;
    determining whether the test agent increases or induces a p21 signal transduction pathway component; and
    correlating the ability of the test agent to increase expression, activity or levels of the p21 signal transduction pathway component with the agent's ability to reduce the appearance or formation of wrinkles,
    thereby screening for an agent that reduces the appearance or formation of wrinkles.

2. The method of claim 1, further comprising selecting a test agent that increases expression, activity or levels of the p21 signal transduction pathway component.

3. The method of claim 1, wherein the determining step comprises determining if the test agent increases or induces p21.

4. The method of claim 3, wherein the determining step comprises:
    (a) providing a cell, tissue or non-human subject comprising an exogenous nucleic acid comprising a p21 regulatory region operably linked to a nucleotide sequence encoding a reporter polypeptide; and
    (b) evaluating the ability of the test agent to increase the activity of the reporter polypeptide in the cell, tissue or non-human subject,
    wherein the test agent is determined to increase or induce p21 if it increases the activity of the reporter polypeptide.

5. The method of claim 1, wherein the test agent is selected from the group consisting of: an animal extract, a botanical extract, a fungal extract, a small molecule, a protein, a lipid, and a nucleic acid.

6. The method of claim 1, wherein the determining step comprises:
   (a) providing a cell, tissue or non-human subject comprising an exogenous nucleic acid comprising a regulatory region of the p21 signal transduction pathway component operably linked to a nucleotide sequence encoding a reporter polypeptide; and
   (b) evaluating the ability of the test agent to increase the activity of the reporter polypeptide in the cell, tissue or non-human subject,
   wherein the test agent is determined to increase or induce the p21 signal transduction pathway component if the test agent increases the activity of the reporter polypeptide.

7. The method of claim 6, wherein the evaluating step comprises topically administering the agent to the skin of the subject.

8. The method of claim 6, wherein the subject is an experimental animal.

9. The method of claim 1 that comprises topically administering the test agent to UVB-irradiated skin, and evaluating ability of the test agent to reduce the formation or appearance of wrinkles.

* * * * *